United States Patent
Takeshima

(10) Patent No.: US 12,399,234 B2
(45) Date of Patent: Aug. 26, 2025

(54) PHYSICAL SIMULATION APPARATUS AND METHOD

(71) Applicant: Canon Medical Systems Corporation, Otawara (JP)

(72) Inventor: Hidenori Takeshima, Tokyo (JP)

(73) Assignee: Canon Medical Systems Corporation, Otawara (JP)

( * ) Notice: Subject to any disclaimer, the term of this patent is extended or adjusted under 35 U.S.C. 154(b) by 282 days.

(21) Appl. No.: 18/330,469

(22) Filed: Jun. 7, 2023

(65) Prior Publication Data

US 2023/0400532 A1 Dec. 14, 2023

(30) Foreign Application Priority Data

Jun. 8, 2022 (JP) .................................. 2022-093108
Apr. 28, 2023 (JP) .................................. 2023-074903

(51) Int. Cl.
*G01R 33/00* (2006.01)
*G01R 33/48* (2006.01)

(52) U.S. Cl.
CPC ......... *G01R 33/0064* (2013.01); *G01R 33/48* (2013.01)

(58) Field of Classification Search
None
See application file for complete search history.

(56) References Cited

FOREIGN PATENT DOCUMENTS

| JP | 2017-140165 A | 8/2017 |
|---|---|---|
| JP | 2020-149131 A | 9/2020 |

OTHER PUBLICATIONS

Stocker et al., "High-Performance Computing MRI Simulations", Magnetic Resonance in Medicine, vol. 64, 2010, 8 pages.
Liu et al., "Fast Realistic MRI Simulations Based on Generalized Multi-Pool Exchange Tissue Model", IEEE Transactions on Medical Imaging, vol. 36, No. 2, 2017, 29 pages.
Kose et al., "BlochSolver: A GPU-optimized fast 3D MRI simulator for experimentally compatible pulse sequences", Journal of Magnetic Resonance, vol. 281, 2017, 15 pages.

*Primary Examiner* — Rodney E Fuller
(74) *Attorney, Agent, or Firm* — Oblon, McClelland, Maier & Neustadt, L.L.P.

(57) ABSTRACT

A physical simulation apparatus includes element reception circuitry, a storage device, storage control circuitry, and simulation circuitry. The element reception circuitry successively receives sequence elements of a hardware control sequence that is divided according to a division rule on a transmission side. The storage device stores the received sequence elements. The storage control circuitry reads out the sequence elements stored in the storage device, in a case where a separately determined condition is satisfied. The simulation circuitry executes a physical simulation, based on the read-out sequence elements, and computes a predicted computation value of a signal value that a control target apparatus of the sequence elements collects.

14 Claims, 10 Drawing Sheets

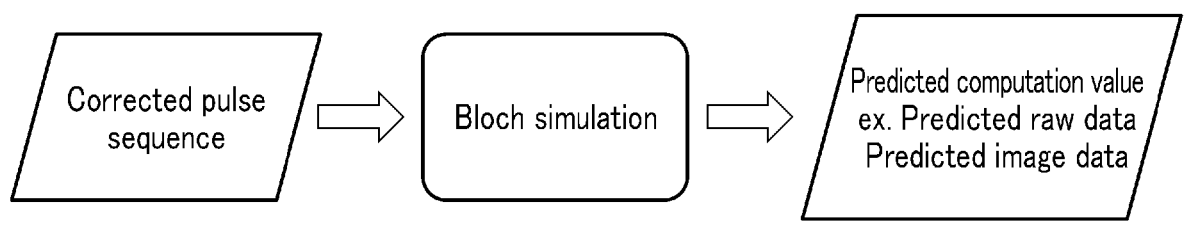
F I G. 3

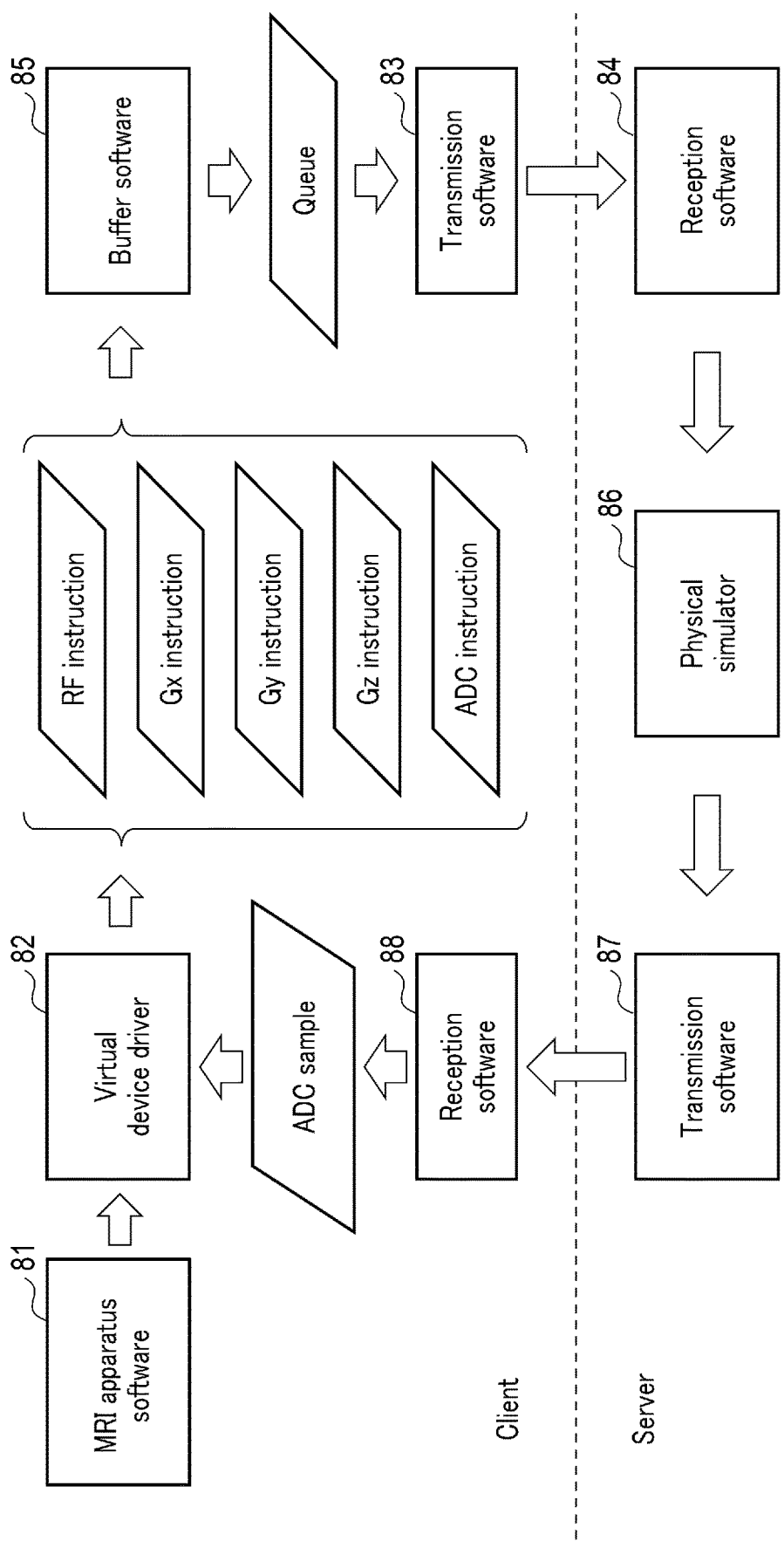
F I G. 9

PHYSICAL SIMULATION APPARATUS AND METHOD

CROSS-REFERENCE TO RELATED APPLICATIONS

This application is based upon and claims the benefit of priority from prior Japanese Patent Application No. 2022-093108, filed Jun. 8, 2022, and NO. 2023-074903, filed Apr. 28, 2023; the entire contents of all of which are incorporated herein by reference.

FIELD

Embodiments described herein relate generally to a physical simulation apparatus and method.

BACKGROUND

In the field of magnetic resonance imaging, there is a Bloch simulation apparatus that simulates Bloch equations. The Bloch simulation apparatus receives the entirety of a pulse sequence, and executes a Bloch simulation, based on the received pulse sequence. At this time, the Bloch simulation apparatus executes a process by accessing each element constituting the pulse sequence, in an order that is convenient for enhancing its own computation speed. In other words, the computation speed is enhanced by utilizing information that is considered inaccessible by actual hardware at a time of simulation.

BRIEF DESCRIPTION OF THE DRAWINGS

FIG. 3 is a diagram illustrating an input/output of a Bloch simulation according to the first embodiment.

FIG. 9 is a diagram illustrating a software configuration and a flow of various data relating to a Bloch simulation according to Example 2.

DETAILED DESCRIPTION

According to one embodiment, a physical simulation apparatus includes element reception circuitry, a storage device, storage control circuitry, and simulation circuitry. The element reception circuitry is configured to successively receive sequence elements of a hardware control sequence that is divided according to a division rule on a transmission side. The storage device is configured to store the received sequence elements. The storage control circuitry is configured to read out the sequence elements stored in the storage device, in a case where a separately determined condition is satisfied. The simulation circuitry is configured to execute a physical simulation, based on the read-out sequence elements, and to compute a predicted computation value of a signal value that a control target apparatus of the sequence elements collects.

Hereinafter, embodiments of a physical simulation apparatus, method and program are described in detail with reference to the accompanying drawings.

First Embodiment

Figure 1:
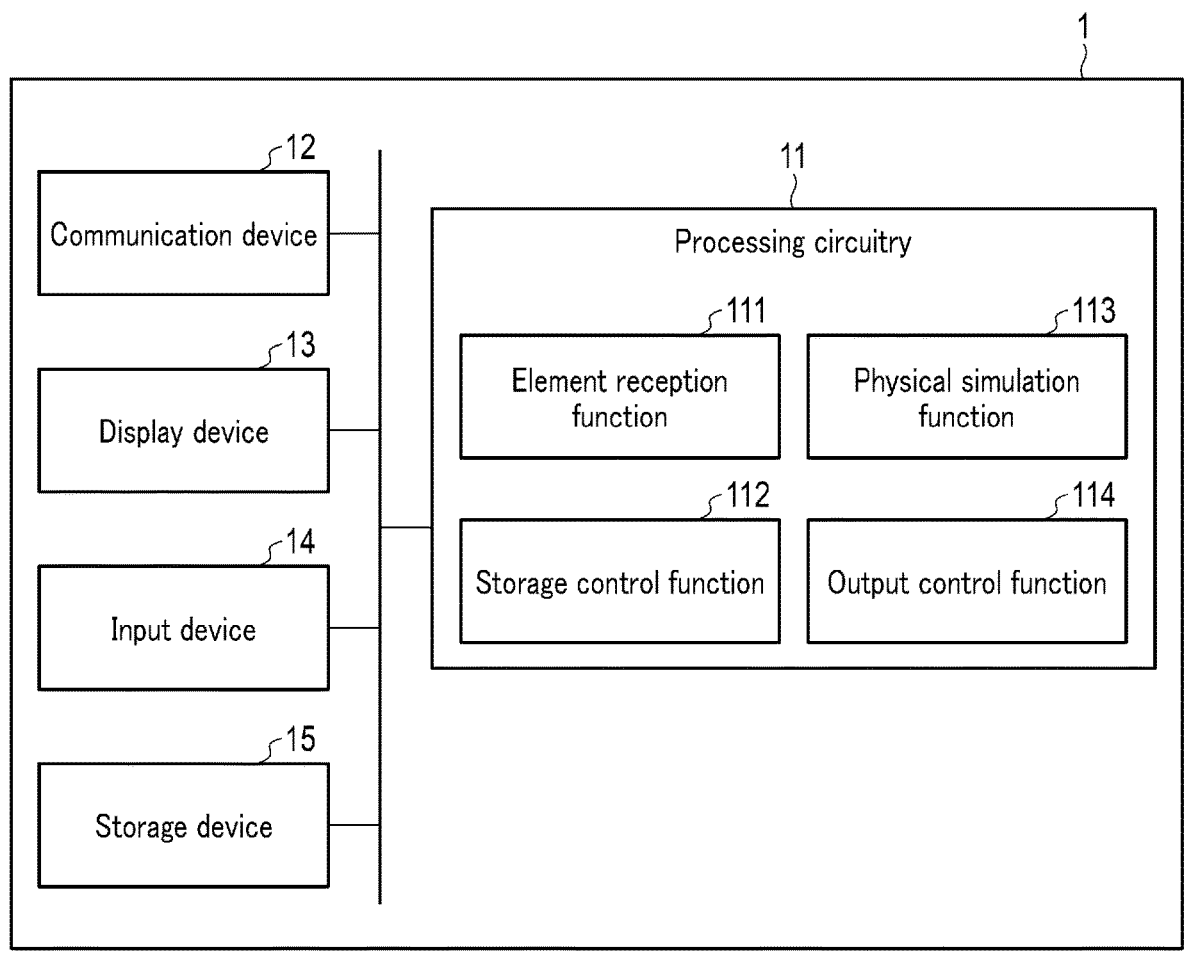
FIG. 1 is a diagram illustrating a configuration example of a physical simulation apparatus according to a first embodiment.

FIG. 1 is a diagram illustrating a configuration example of a physical simulation apparatus 1 according to a first embodiment. As illustrated in FIG. 1, the physical simulation apparatus 1 is a computer including processing circuitry 11, a communication device 12, a display device 13, an input device 14 and a storage device 15. Data communication between the processing circuitry 11, communication device 12, display device 13, input device 14 and storage device 15 is executed via a bus.

The processing circuitry 11 includes a processor such as a CPU (Central Processing Unit). An element reception function 111, a storage control function 112, a physical simulation function 113 and an output control function 114 are implemented by the processor starting a physical simulation program installed in the storage device or the like. The functions 111 to 114 are not necessarily implemented by single processing circuitry. A plurality of independent processors may be combined to constitute processing circuitry, and the respective processors may implement the functions 111 to 114 by executing the physical simulation program. In addition, the functions 111 to 114 may be implemented as modules constituting the physical simulation program, or may be implemented as individual hardware.

By the element reception function 111, the processing circuitry 11 successively receives sequence elements of a hardware control sequence that is divided according to a division rule on a transmission side. The sequence elements may be transmitted from a control target apparatus of the hardware control sequence, or may be transmitted from a computer that is different from the control target apparatus. In addition, the hardware control sequence may be generated by the control target apparatus, or may be generated by a computer that is different from the control target apparatus. Furthermore, the hardware control sequence may be divided into sequence elements by the control target apparatus, or may be divided into sequence elements by some other computer. The division rule on the transmission side means a rule of division, which is adopted by a computer that divides the hardware control sequence into sequence elements. The received sequence elements are temporarily stored in the storage device 15.

By the storage control function 112, the processing circuitry 11 controls read and write of various data from and to the storage device 15. For example, in a case where a separately determined condition is satisfied, the processing circuitry 11 reads out the sequence elements stored in the storage device 15.

By the physical simulation function 113, the processing circuitry 11 executes a physical simulation, based on the read-out sequence elements, and computes a predicted computation value of a signal value that the control target apparatus of the sequence elements collects. The type of the control target apparatus may be any type if the control target apparatus can operate according to the hardware control sequence. It is assumed that the type of the control target apparatus according to the present embodiment is, by way of example, a medical image diagnosis apparatus, such as a magnetic resonance imaging apparatus, an X-ray computed tomography apparatus, an ultrasonic diagnosis apparatus, or a nuclear medicine diagnosis apparatus.

By the implementation of the output control function 114, the processing circuitry 11 outputs various data. For example, the processing circuitry 11 displays various data on the display device 13, or transmits various data to some other computer or the like via the communication device 12.

The communication device 12 is an interface for connection to a medical apparatus, an examination apparatus, a workstation, a PACS (Picture Archiving and Communication System), a HIS (Hospital Information System), an RIS (Radiology Information System), or the like, via a LAN (Local Area Network) or the like. The communication device 12 transmits and receives various data to and from a connection destination.

The display device 13 displays various data in accordance with the output control function 114 of the processing circuitry 11. As the display device 13, use can be made of, as appropriate, a liquid crystal display (LCD), a cathode ray tube (CRT) display, an organic electro-luminescence (EL) display (OELD), a plasma display, or some other freely chosen display. Besides, the display device 13 may be a projector.

The input device 14 accepts various input operations from a user, converts an accepted input operation to an electric signal, and outputs the electric signal to the processing circuitry 11. Specifically, the input device 14 is connected to input devices such as a mouse, a keyboard, a trackball, a switch, a button, a joystick, a touchpad, and a touch panel display. The input device 14 outputs to the processing circuitry 11 an electric signal corresponding to an input operation to the input device 14. In addition, the input device 14 may be an input device provided in some other computer that is connected via a network or the like. The input device 14 may be a speech recognition device that converts a voice signal collected by a microphone into an instruction signal.

The storage device 15 is a storage device that stores various data, such as a ROM (Read Only Memory), a RAM (Random Access Memory), an HDD (Hard Disk Drive), an SSD (Solid State Drive), an integrated circuit storage device, or the like. The storage device 15 stores, for example, a physical simulation program or the like. The storage device 15 may be, aside from the above-mentioned storage devices, a portable storage medium such as a CD (Compact Disc), a DVD (Digital Versatile Disc) or a flash memory, or a drive device that reads and writes various information from and to a semiconductor memory element or the like. The storage device 15 may be provided in some other computer that is connected to the physical simulation apparatus 1 via a network.

Hereinafter, the physical simulation apparatus 1 according to the first embodiment is described in detail. In the description below, it is assumed that the control target apparatus that is the control target of the hardware control sequence is a magnetic resonance imaging apparatus, and the hardware control sequence is a pulse sequence.

Figure 2:
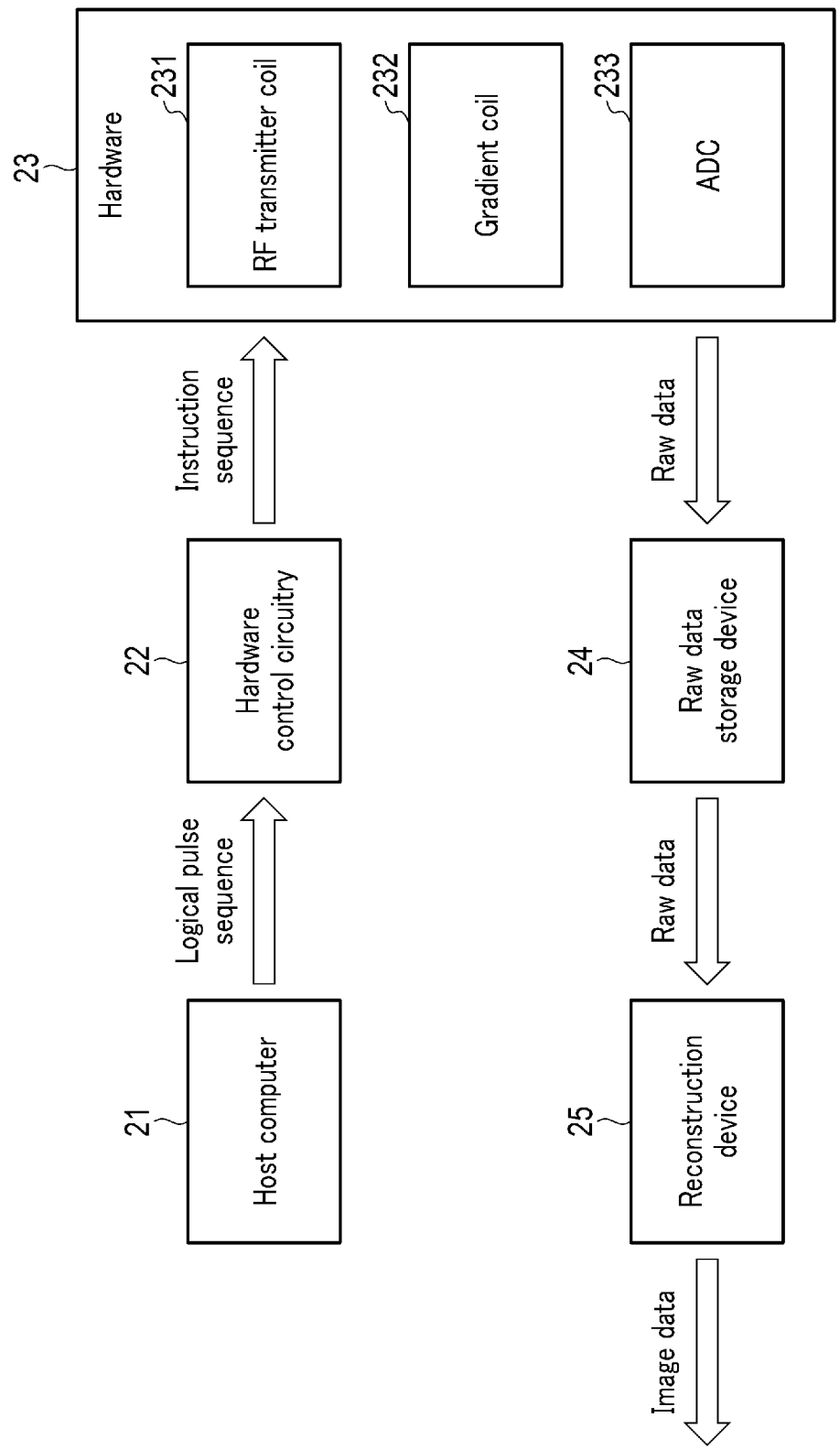
FIG. 2 is a diagram illustrating a hardware configuration and a flow of various data relating to MR imaging of a magnetic resonance imaging apparatus according to the first embodiment.

FIG. 2 is a diagram illustrating a hardware configuration and a flow of various data relating to MR imaging of the magnetic resonance imaging apparatus. As illustrated in FIG. 2, a host computer 21 first generates a logical pulse sequence. The logical pulse sequence means an original pulse sequence. Specifically, the logical pulse sequence represents a transmission RF magnetic field and a gradient of gradient magnetic fields before execution of a process corresponding to hardware, and a time-series waveform of an MR signal. The logical pulse sequence is transmitted to hardware control circuitry 22. The hardware control circuitry 22 interprets the logical pulse sequence, and converts the logical pulse sequence to an instruction sequence that is suited to the hardware. The instruction sequence means a sequence of instructions to hardware used in MR imaging, for implementing the logical pulse sequence. The instruction sequence is transmitted to hardware 23.

As illustrated in FIG. 2, the hardware 23 includes, for example, constituent devices (hereinafter "control target constituent devices") such as an RF transmitter coil 231, a gradient coil 232, and A/D conversion circuitry (ADC: analog-to-digital converter) 233. The control target constituent devices (RF transmitter coil 231, gradient coil 232 and ADC 233) cooperate according to the instruction sequence, and execute MR imaging.

The hardware control circuitry 22 corresponding to the RF transmitter coil 231 is transmission circuitry. The transmission circuitry supplies a driving signal to the transmitter coil, and generates an RF transmission pulse corresponding to the driving signal from the RF transmitter coil 231. The hardware control circuitry 22 corresponding to the gradient coil 232 is a gradient magnetic field power supply. The gradient magnetic field power supply supplies a driving signal to the gradient coil 232, and generates a gradient magnetic field from the gradient coil 232. The gradient coil 232 includes a Gz coil that generates a slice selection gradient magnetic field, a Gy coil that generates a phase encoding gradient magnetic field, and a Gx coil that generates a frequency encoding gradient magnetic field. The hardware control circuitry 22 corresponding to the ADC 233 is ADC control circuitry. The ADC control circuitry supplies a driving signal to the ADC 233, and causes the ADC 233 to execute AD conversion. The ADC 233 generates raw data by applying AD conversion to an MR signal received by a receiver coil, in accordance with the driving signal from the ADC control circuitry. Specifically, by sampling the MR signal at fixed cycles, specifying amplitude values of the MR signal at sampling points, and quantizing the specified amplitude values, the amplitude values are digitized. The digitized amplitude values are stored as raw data in a raw data storage device 24. The raw data that fills a k space is also called "k space data". A reconstruction device 25 reads out the raw data, such as k space data, from the raw data storage device 24, applies a reconstruction process to the raw data, and reconstructs image data.

In the field of magnetic resonance imaging, an MRI simulator is used as a physical simulation that simulates MR imaging. As one example of the physical simulation that simulates MR imaging, there is known a Bloch simulation that simulates Bloch equations (or Bloch-Torrey equations or Bloch-McConnell equations). In the Bloch simulation, an isochromat in a micro-voxel is computed according to Broch equations, and a predicted computation value of k space data due to the isochromat can be computed. Specifically, as the predicted computation value, a predicted value of k space data that is raw data, or a predicted value of image data, is computed.

In the general Bloch simulation, the entirety of the logical pulse sequence is received, and, based on the received logical pulse sequence, a Bloch simulation is executed. At this time, the Bloch simulation executes a process by accessing the logical pulse sequence in an order that is convenient for enhancing its own computation speed. In other words, the computation speed is enhanced by utilizing information that is considered inaccessible by actual hardware at a time of simulation. Thus, there is room for an improvement from the standpoint of reproducibility of MR imaging.

FIG. 3 is a diagram illustrating an input/output of the Bloch simulation according to the first embodiment. As illustrated in FIG. 3, in the Bloch simulation according to the first embodiment, a predicted computation value is computed based on not the logical pulse sequence, but a corrected pulse sequence. The corrected pulse sequence is generated based on the logical pulse sequence. The corrected pulse sequence is a sequence obtained by processing the logical pulse sequence, such that the Bloch simulation is executed according to a processing order of the pulse sequence or instruction sequence at a time when the hardware 23 executes MR imaging.

Figure 4:
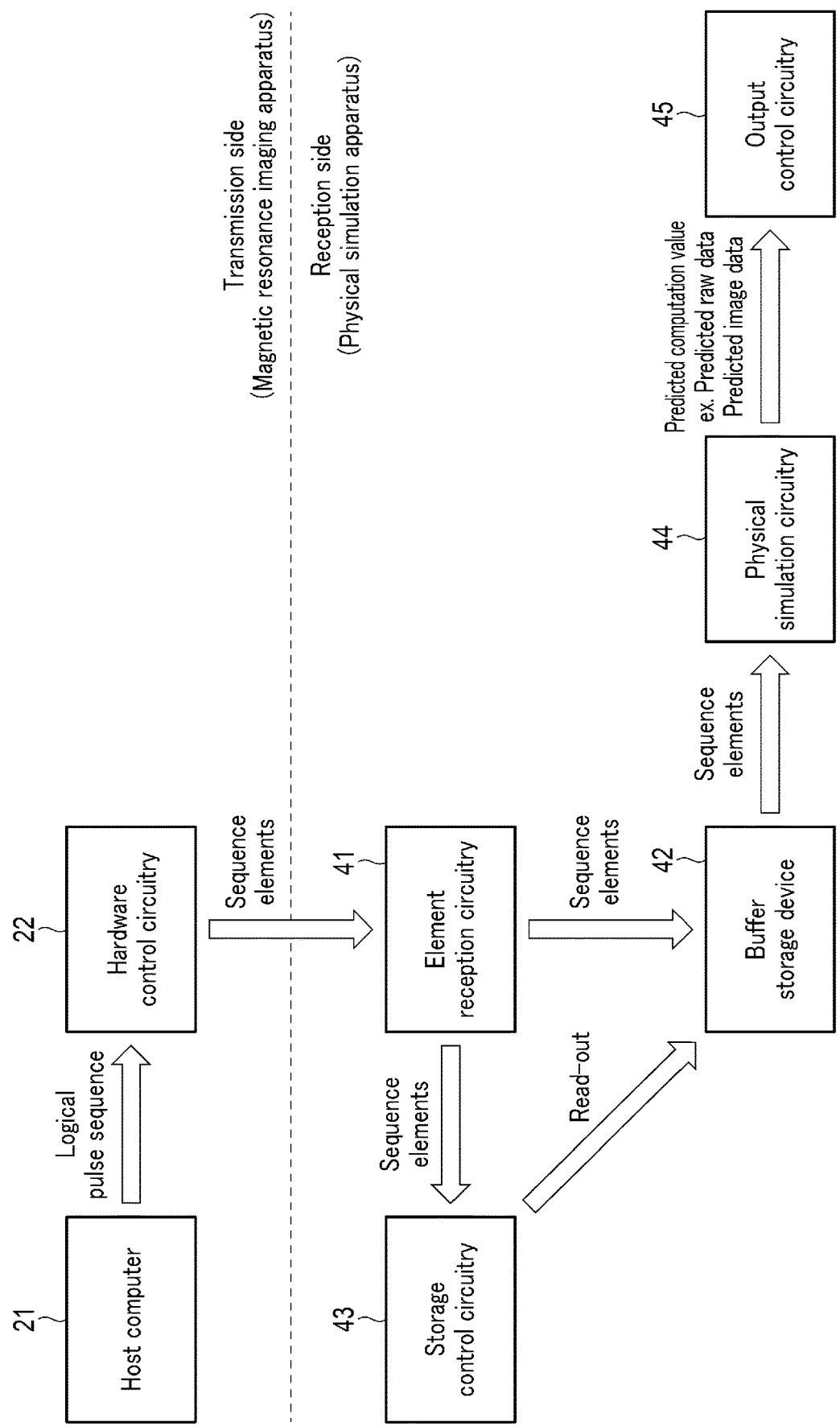
FIG. 4 is a diagram illustrating a hardware configuration and a flow of various data relating to a Bloch simulation according to the first embodiment.

Hereinafter, referring to FIG. 4, a description is given of a hardware configuration and a processing procedure of the physical simulation apparatus 1 according to the first embodiment. FIG. 4 is a diagram illustrating a hardware configuration and a flow of various data relating to the Bloch simulation according to the first embodiment. As illustrated in FIG. 4, the hardware configuration relating to the Bloch simulation according to the first embodiment is separated into a transmission side and a reception side of pulse sequence information. It is assumed that the transmission side is the magnetic resonance imaging apparatus, the reception side is the physical simulation apparatus, and the magnetic resonance imaging apparatus and the physical simulation apparatus are connected via network communication.

The magnetic resonance imaging apparatus includes the host computer 21 and hardware control circuitry 22. The host computer 21 and hardware control circuitry 22 may be accommodated in a single housing, or may be accommodated in separate housings. The physical simulation apparatus 1 includes element reception circuitry 41, a buffer storage device 42, storage control circuitry 43, physical simulation circuitry 44, and output control circuitry 45. The element reception circuitry 41, buffer storage device 42, storage control circuitry 43, physical simulation circuitry 44 and output control circuitry 45 are connected by interprocess communication (PCI: peripheral component interconnect). The element reception circuitry 41, storage control circuitry 43, physical simulation circuitry 44 and output control circuitry 45 are implementations as circuitry of the element reception function 111, storage control function 112, physical simulation function 113 and output control function 114. The buffer storage device 42 is an example of the storage device 15.

The host computer 21 generates a logical pulse sequence and transmits the logical pulse sequence to the hardware control circuitry 22. The hardware control circuitry 22 divides the logical pulse sequence according to a predetermined division rule on the transmission side, and converts the logical pulse sequence into a series of a plurality of sequence elements. The division rule may be identical to, or different from, the conversion rule from the logical pulse sequence into the corrected pulse sequence. In addition, the content of the division rule is not particularly limited. For example, the hardware control circuitry 22 divides the logical pulse sequence in a time-series manner, and/or divides the logical pulse sequence in regard to each control target constituent device, and converts the logical pulse sequence into a series of a plurality of sequence elements.

Figure 5:
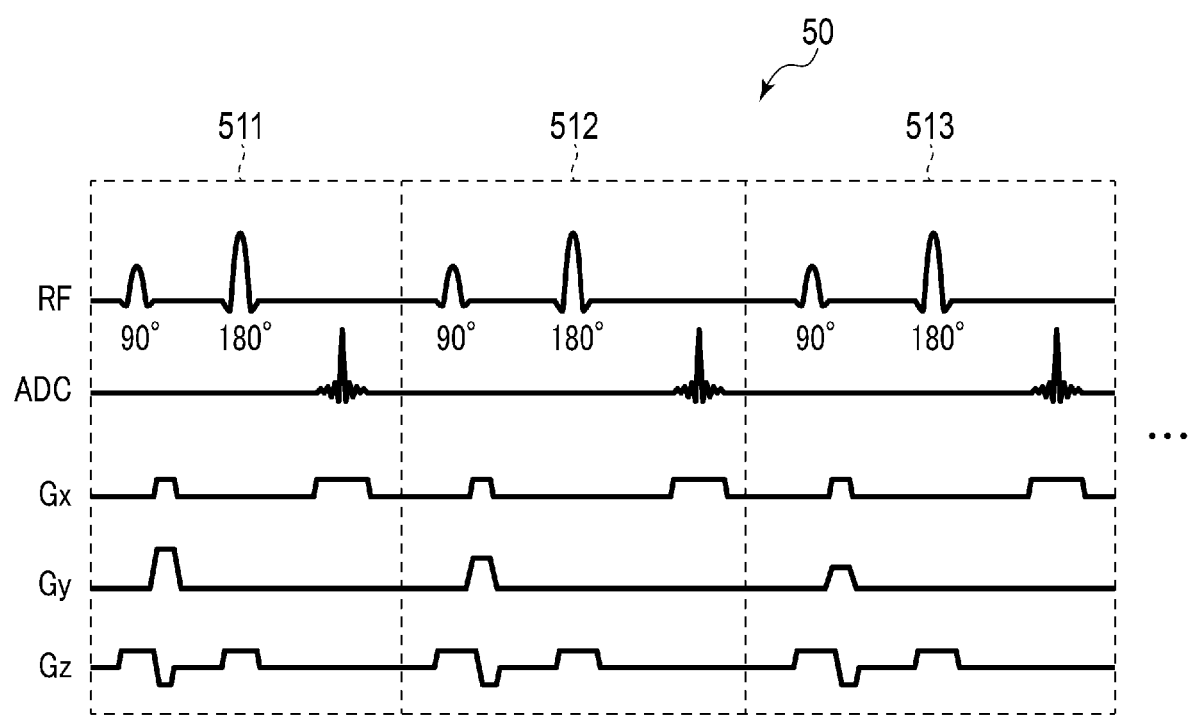
FIG. 5 is a diagram exemplarily illustrating a logical pulse sequence and sequence elements.

FIG. 5 is a diagram exemplarily illustrating a logical pulse sequence 50 and sequence elements 511, 512 and 513. As the logical pulse sequence 50, a pulse sequence of a spin echo method is exemplarily illustrated, but the logical pulse sequence 50 is not limited to this, and may be a pulse sequence of a gradient echo method, or a pulse sequence of an imaging method that applies or modifies the spin echo method or gradient echo method, or any other pulse sequence.

As illustrated in FIG. 5, the logical pulse sequence 50 represents a time-series waveform in regard to each control target constituent device. "RF" represents a time-series waveform of RF pulses applied by the RF transmitter coil 231 that is driven in accordance with a driving signal from the transmission circuitry. "ADC" represents a time-series waveform of an MR signal received via the receiver coil. "Gz" represents a time-series waveform of a gradient of a slice selection gradient magnetic field that is applied by a Gz coil (one example of the gradient coil 232) that is driven in accordance with a driving signal from the gradient magnetic field power supply. "Gy" represents a time-series waveform of a gradient of a phase encoding gradient magnetic field that is applied by a Gy coil (one example of the gradient coil 232) that is driven in accordance with a driving signal from the gradient magnetic field power supply. "Gx" represents a time-series waveform of a gradient of a frequency encoding gradient magnetic field that is applied by a Gx coil (one example of the gradient coil 232) that is driven in accordance with a driving signal from the gradient magnetic field power supply.

As illustrated in FIG. 5, for example, the logical pulse sequence 50 is divided into a plurality of sequence elements 511, 512, 513, . . . , in a time series. Each sequence element 511, 512, 513 can be expressed as a fragment of the logical pulse sequence (hereinafter "sequence fragment"). Each sequence fragment 511, 512, 513 illustrated in FIG. 5 includes time-series waveforms of all control target constituent devices. In other words, each sequence fragment 511, 512, 513 is not divided in regard to each control target constituent device. The division rule in this case is set to be that the logical pulse sequence 50 is divided in a time series. The time width of each sequence fragment 511, 512, 513 may be divided in any time unit. For example, as illustrated in FIG. 5, each sequence fragment 511, 512, 513 may be divided in units of a repetition time TR (time of repetition) that is a time width from the application of a 90-degree pulse to the reception of an MR signal. In another example, each sequence fragment 511, 512, 513 may be divided in units of a plurality of TRs.

The logical pulse sequence 50 may further be divided in regard to each control target constituent device. For example, the logical pulse sequence 50 may be divided in regard to each of "RF", "Gz", "Gy", "Gx" and "ADC". Alternatively, the logical pulse sequence 50 may be divided in regard to each of combinations of control target constituent devices. Examples of the combination of control target constituent devices include a combination of "Gz", "Gy" and "Gx", a combination of "Gz", "Gy", "Gx" and "RF", and a combination of "RF" and "ADC". In another example, the logical pulse sequence 50 may be divided in a time series and in regard to each control target constituent device.

In the above-described embodiment, the sequence element was described as the sequence fragment that is obtained by dividing the logical pulse sequence 50 in the time series and/or in regard to each control target constituent device. However, the content of the sequence element is not limited to this. For example, the sequence element may be an instruction sequence corresponding to the sequence fragment. The instruction sequence is a sequence of instructions for implementing each time-series waveform included in the sequence fragment, in regard to a control target constituent device corresponding to the time-series waveform. For example, in regard to the transmitter coil in FIG. 5, the sequence of instructions is "generate a 90-degree pulse" and "generate a 180-degree pulse". Fragments of the instruction sequence (hereinafter "instruction fragments") may be fragments obtained by strictly dividing the logical pulse sequence in an order of time, or may be fragments in which specific instruction fragments are recombined reversely to time from the standpoint of a computation efficiency or the like.

As illustrated in FIG. 4, the hardware control circuitry 22 successively transmits the sequence elements to the element reception circuitry 41 of the physical simulation apparatus 1 via network communication. The order of transmission of sequence elements may be set, for example, based on the order of processing by the physical simulation circuitry 44. Typically, the sequence elements may be transmitted in the order of time from the start to the end of the logical pulse sequence.

The element reception circuitry 41 successively receives the sequence elements of the logical pulse sequence, which are divided according to the division rule on the transmission side and are transmitted from the hardware control circuitry 22 of the magnetic resonance imaging apparatus. The element reception circuitry 41 is connected to the hardware control circuitry 22 via network communication. The "reception" in the present embodiment means the reception of sequence elements that are actively transmitted from the magnetic resonance imaging apparatus. In other words, in the present embodiment, it is not assumed that the element reception circuitry 41 requests, from the magnetic resonance imaging apparatus, the format of sequence elements and the division rule of a design sequence. The sequence elements are supplied to the buffer storage device 42.

The buffer storage device 42 temporarily stores the sequence elements received by the element reception circuitry 41.

The storage control circuitry 43 reads out the sequence elements stored in the buffer storage device 42, if a separately determined condition (hereinafter "read condition") is satisfied. The content of the read condition is set in such a manner as to reproduce the operation of the hardware in the MR imaging. Normally, raw data or image data is not generated until an instruction to the ADC 233 is issued. Thus, in one example, the read condition is preferably set to be that a start instruction or an end instruction of sampling by the ADC 233 is received. In another example, the read condition may be set to be that a predetermined time has passed since a start instruction or an end instruction of sampling by the ADC 233. The read-out sequence element is supplied to the physical simulation circuitry 44.

In a case where the storage control circuitry 43 receives the sequence elements from the element reception circuitry 41, the storage control circuitry 43 stands by for the satisfaction of the read condition by analyzing the sequence elements. If the read condition is satisfied, the storage control circuitry 43 reads out the sequence elements stored in the buffer storage device 42, and supplies the sequence elements to the physical simulation circuitry 44. For example, a description is given of a case where the read condition is set to be that a start instruction of sampling by the ADC 233 is received. In this case, the storage control circuitry 43 searches for the start instruction of sampling by analyzing the sequence elements in a time series. Then, if the start instruction is detected, it is determined that the read condition is satisfied. By using the detection of the start instruction as a trigger, the storage control circuitry 43 reads out all sequence elements stored in the buffer storage device 42, and supplies the sequence elements to the physical simulation circuitry 44.

In another example, a description is given of a case where the read condition is set to be that a predetermined time (hereinafter "set time") has passed since the end instruction of sampling by the ADC 233. In this case, the storage control circuitry 43 searches for the end instruction of sampling by analyzing the sequence elements in a time series. Then, by using the detection of the end instruction as a trigger, the storage control circuitry 43 measures an elapsed time from a time point at which the end instruction is detected, and detects that the elapsed time reaches the set time. If it is detected that the elapsed time reaches the set time, it is determined that the read condition is satisfied. By using as a trigger the fact that the elapsed time reaches the set time, the storage control circuitry 43 reads out all sequence elements stored in the buffer storage device 42, and supplies the sequence elements to the physical simulation circuitry 44. The same process is executed for other read conditions.

The physical simulation circuitry 44 executes a Bloch simulation, based on the sequence elements supplied from the buffer storage device 42, and computes predicted raw data and/or predicted image data that is a predicted computation value of raw data and/or image data that the ADC collects. Specifically, each time a sequence element is supplied, the physical simulation circuitry 44 executes an arithmetic operation of Bloch equations, based on the sequence element. For example, the Bloch equations can be expressed by logical equations indicated in (1), (2) and (3) below. Note that γ is a gyro-magnetic ratio; M is an isochromat; $M_x$ is an x component of the isochromat M; $M_y$ is a y component of the isochromat M; $M_z$ is a z component of the isochromat M; $M_0$ is a z component of the isochromat M in an equilibrium state; $T_2$ is a T2 relaxation time; $T_1$ is a $T_1$ relaxation time; B is a magnetic field; $B_x$ is an x component of the magnetic field B; $B_y$ is a y component of the magnetic field B; $B_z$ is a z component of the magnetic field B; and $B_0$ is a z component of the magnetic field B in an equilibrium state. The physical simulation circuitry 44 computes transverse magnetization components $M_x$ and $M_y$ by computing equations (1), (2) and (3) or approximate equations equivalent to equations (1), (2) and (3) for each time step width dt, based on the sequence elements. The transverse magnetization components $M_x$ and $M_y$ are synonymous with predicted computation values of the MR signal. A predicted computation value (predicted raw data) of k space data is acquired by computing the transverse magnetization components $M_x$ and $M_y$, based on the sequence element for one TR. The physical simulation circuitry 44 generates predicted image data by applying a reconstruction process to predicted raw data.

$$dM_x/dt = \gamma(M \times B)_x - (M_x/T_2) \qquad (1)$$

$$dM_y/dt = \gamma(M \times B)_y - (M_y/T_2) \qquad (2)$$

$$dM_z/dt = \gamma(M \times B)_z - \{(M_z - M_0)/T_1\} \qquad (3)$$

$M=(M_x, M_y, M_z)$
$B=(B_x, B_y, B_0+\Delta B_z)$

In a case where the elapsed time of the Bloch simulation is slower than a predetermined time, the physical simulation circuitry 44 may lower the accuracy of the Bloch simulation. In one example, in order to lower the accuracy of the Bloch simulation, the physical simulation circuitry 44 increases the time step width dt in the Bloch simulation. For example, by doubly increasing the time step width, the computation amount can be reduced to ½. The predetermined time may be set to a freely selected value by a user or the like.

The output control circuitry 45 outputs the predicted computation value calculated by the physical simulation circuitry 44 to the outside of the processing circuitry 11. For example, the output control circuitry 45 displays the predicted image data on the display device 13.

By the above, the description of the hardware configuration and processing procedure of the physical simulation apparatus 1 according to the first embodiment has been completed.

As described above, in the general Bloch simulation, the entirety of the logical pulse sequence is received, and, based on the received logical pulse sequence, a Bloch simulation is executed. At this time, the Bloch simulation executes a process by accessing the logical pulse sequence in an order that is convenient for enhancing its own computation speed. In other words, the computation speed is enhanced by utilizing information that is considered inaccessible by actual hardware at a time of simulation. In order to enhance the reproducibility of MR imaging by the Block simulation, it is necessary to execute the Bloch simulation, based on source instructions supplied to the hardware 23. In order to achieve this, it is necessary to process sequential instruction fragments corresponding to the capacity of the buffer storage device mounted in the hardware 23. Note that the term "instruction fragments" means a series of instructions that are obtained by dividing the instruction sequence in predetermined units. If each instruction is sequentially processed, the number of instruction fragments becomes excessively large, the computation load of the Bloch simulation increases, and the computation speed lowers.

Normally, raw data or image data is not generated until an instruction for the ADC 233 is issued. Thus, in other words, there is no need to execute the Bloch simulation for each instruction. An overhead of the Bloch simulation can be reduced by processing batchwise the pulse sequence at a timing when an instruction to the ADC 233 is issued. In the present embodiment, based on the above concept, the division rule, the sequence elements, and the read condition are set. By the above, it becomes possible to execute a physical simulation with a high reproducibility of hardware, compared to conventional art, without greatly reducing the processing speed.

Furthermore, the physical simulation apparatus 1 according to the first embodiment includes the element reception circuitry 41 that successively receives the sequence elements of the hardware control sequence that is divided according to the division rule on the transmission side. Thereby, the physical simulation apparatus 1 according to the first embodiment can be assembled afterward in an existing MR system.

Note that in the above description, it is assumed that the physical simulation apparatus 1 is a computer that is separate from the magnetic resonance imaging apparatus. However, the present embodiment is not limited to this. Specifically, the physical simulation apparatus 1 may be assembled in the magnetic resonance imaging apparatus. In this case, the hardware control circuitry 22 and the element reception circuitry 41 may be connected by PCI communication.

Second Embodiment

A physical simulation apparatus 1 according to a second embodiment includes a function of receiving setting information of an examination target of a physical simulation. Hereinafter, the physical simulation apparatus 1 according to the second embodiment is described. Note that in the description below, constituent elements including substantially the same functions as in the first embodiment are denoted by identical reference signs, and an overlapping description thereof is given only where necessary.

Figure 6:
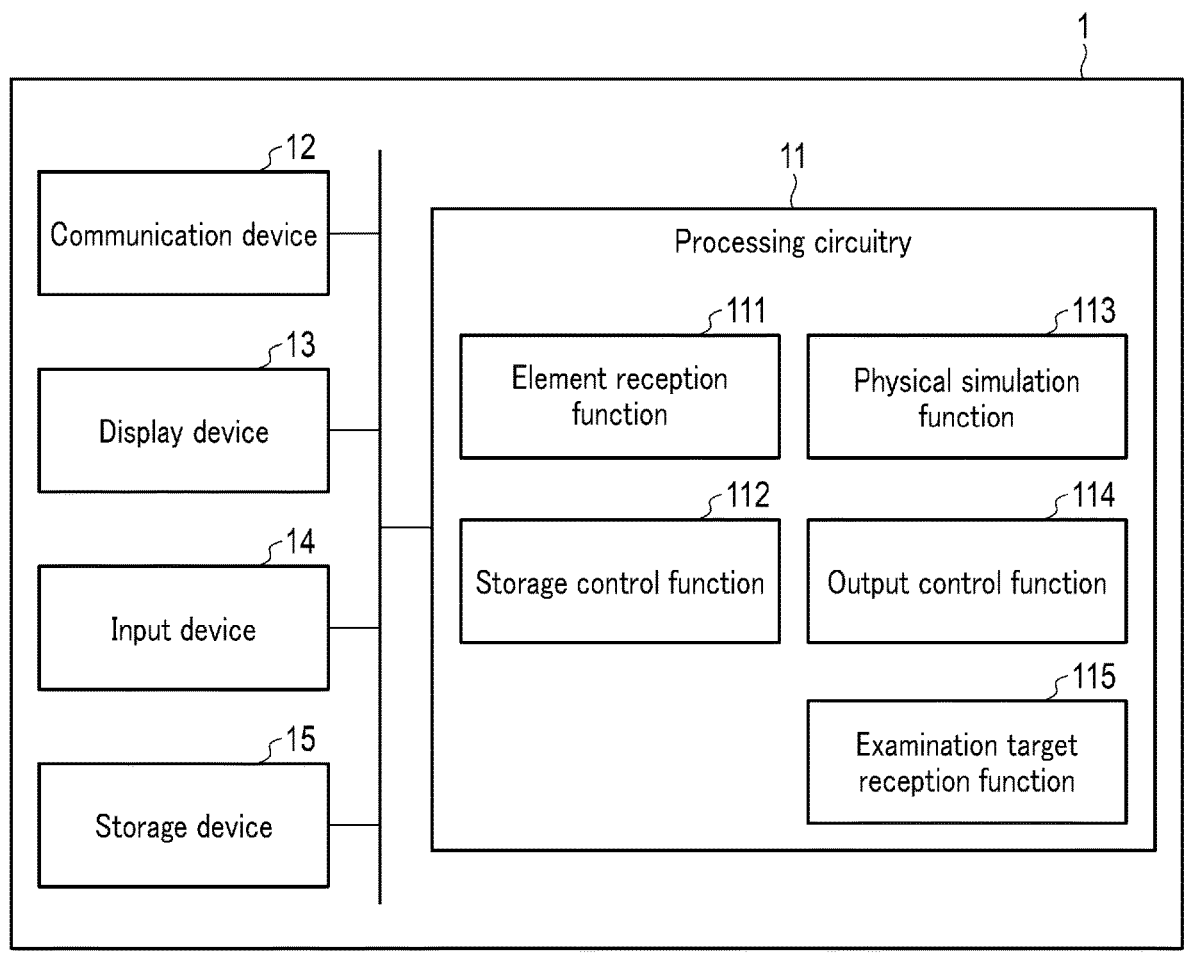
FIG. 6 is a diagram illustrating a configuration example of a physical simulation apparatus according to a second embodiment.

FIG. 6 is a diagram illustrating a configuration example of the physical simulation apparatus 1 according to the second embodiment. As illustrated in FIG. 6, processing circuitry 11 according to the second embodiment implements an examination target reception function 115, in addition to the element reception function 111, storage control function 112, physical simulation function 113 and output control function 114. The functions 111 to 115 are not necessarily implemented by single processing circuitry. A plurality of independent processors may be combined to constitute processing circuitry, and the respective processors may implement the functions 111 to 115 by executing the physical simulation program. In addition, the functions 111 to 115 may be implemented as modules constituting the physical simulation program, or may be implemented as individual hardware.

By the examination target reception function 115, which is a different reception function from the element reception function 111, the processing circuitry 11 receives setting information of an examination target of the physical simulation. The setting information of the examination target is used for the physical simulation.

Hereinafter, the physical simulation apparatus 1 according to the second embodiment is described in detail. In the description below, it is assumed that the control target apparatus that is the control target of the hardware control sequence is a magnetic resonance imaging apparatus. It is also assumed that the physical simulation is a Bloch simulation.

Figure 7:
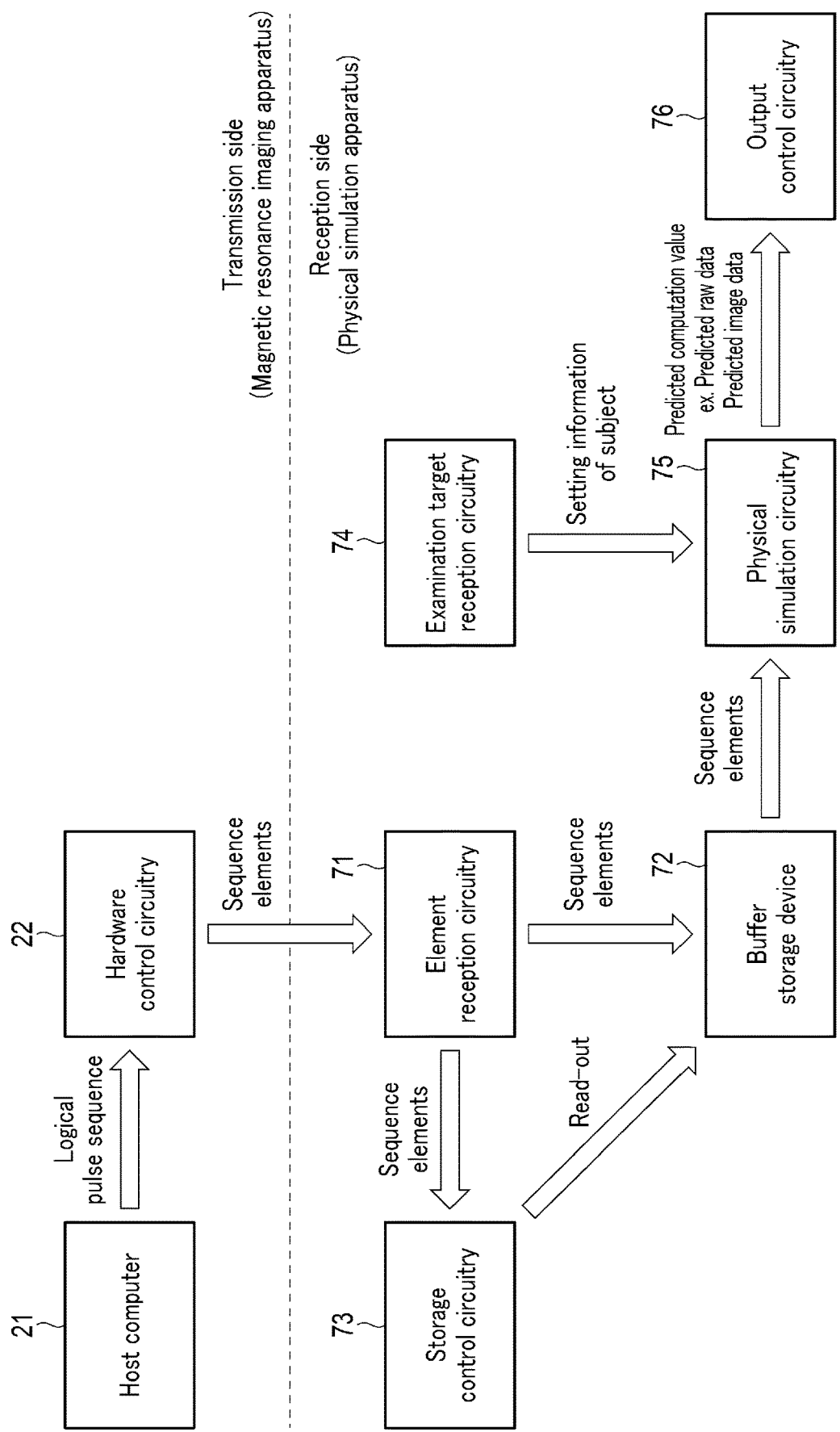
FIG. 7 is a diagram illustrating a hardware configuration and a flow of various data relating to MR imaging of a magnetic resonance imaging apparatus according to the second embodiment.

FIG. 7 is a diagram illustrating a hardware configuration and a flow of various data relating to the Bloch simulation according to the second embodiment. As illustrated in FIG. 7, the physical simulation apparatus 1 on the receiver side includes element reception circuitry 71, a buffer storage device 72, storage control circuitry 73, examination target reception circuitry 74, physical simulation circuitry 75 and output control circuitry 76. The element reception circuitry 71, buffer storage device 72, storage control circuitry 73, examination target reception circuitry 74, physical simulation circuitry 75 and output control circuitry 76 are connected by PCI communication. Since the structures and processes of the element reception circuitry 71, buffer storage device 72, storage control circuitry 73 and output control circuitry 76 are similar to those of the element reception circuitry 41, buffer storage device 42, storage control circuitry 43 and output control circuitry 45, a description thereof is omitted. The examination target reception circuitry 74 is an implementation as circuitry of the examination target reception function 115.

The examination target reception circuitry 74 is reception circuitry that is different from the element reception circuitry 71, and receives setting information of a subject that is an examination target of a Bloch simulation. The subject is a phantom or a numerical value phantom simulating a patient. The setting information of the subject includes not only a physical measurement value or an anatomical structure of a phantom or a patient, but also a T1 relaxation time, a T2 relaxation time, a resonance frequency and the like, which are physical parameters of MRI. The setting information may be transmitted from the host computer 21, or may be transmitted via network communication from an apparatus different from the magnetic resonance imaging apparatus. The examination target reception circuitry 74 may be implemented as server software that receives, for example, TCP/IP or inter-process communications.

The subject setting information is not an item that is input in MR imaging. In addition, since the subject setting information is not information included in the set pulse sequence or sequence elements, the element reception circuitry 71 cannot receive the subject setting information. Accordingly, in the physical simulation apparatus 1 according to the second embodiment, the examination target reception circuitry 74, which is different from the element reception circuitry 71, is provided. By providing the examination target reception circuitry 74, the subject setting information can be received by a different system from the sequence elements. Thereby, the setting of the subject can be executed from the outside of the physical simulation apparatus 1. Note that the subject setting information may be input by the user via the input device 14 of the physical simulation apparatus 1.

The physical simulation circuitry 75 executes the Bloch simulation, based on the read-out sequence elements and the subject setting information supplied from the inspection target reception circuitry 74, and computes predicted raw data and/or predicted image data, which is a predicted computation value of raw data and/or image data that the ADC collects.

By the above, the description of the hardware configuration and processing procedure of the physical simulation apparatus 1 according to the second embodiment has been completed.

According to the second embodiment, since the examination target reception circuitry 74, which is the reception circuitry different from the element reception circuitry 71, is provided, the physical simulation apparatus 1 can receive subject examination information that does not need to be set in normal medical imaging.

Next, a description is given of some examples of the software configuration of the Bloch simulation according to the first embodiment. Note that the examples described below are also applicable to the second embodiment by adding software of the examination target reception circuitry 74 as appropriate.

Example 1

Figure 8:
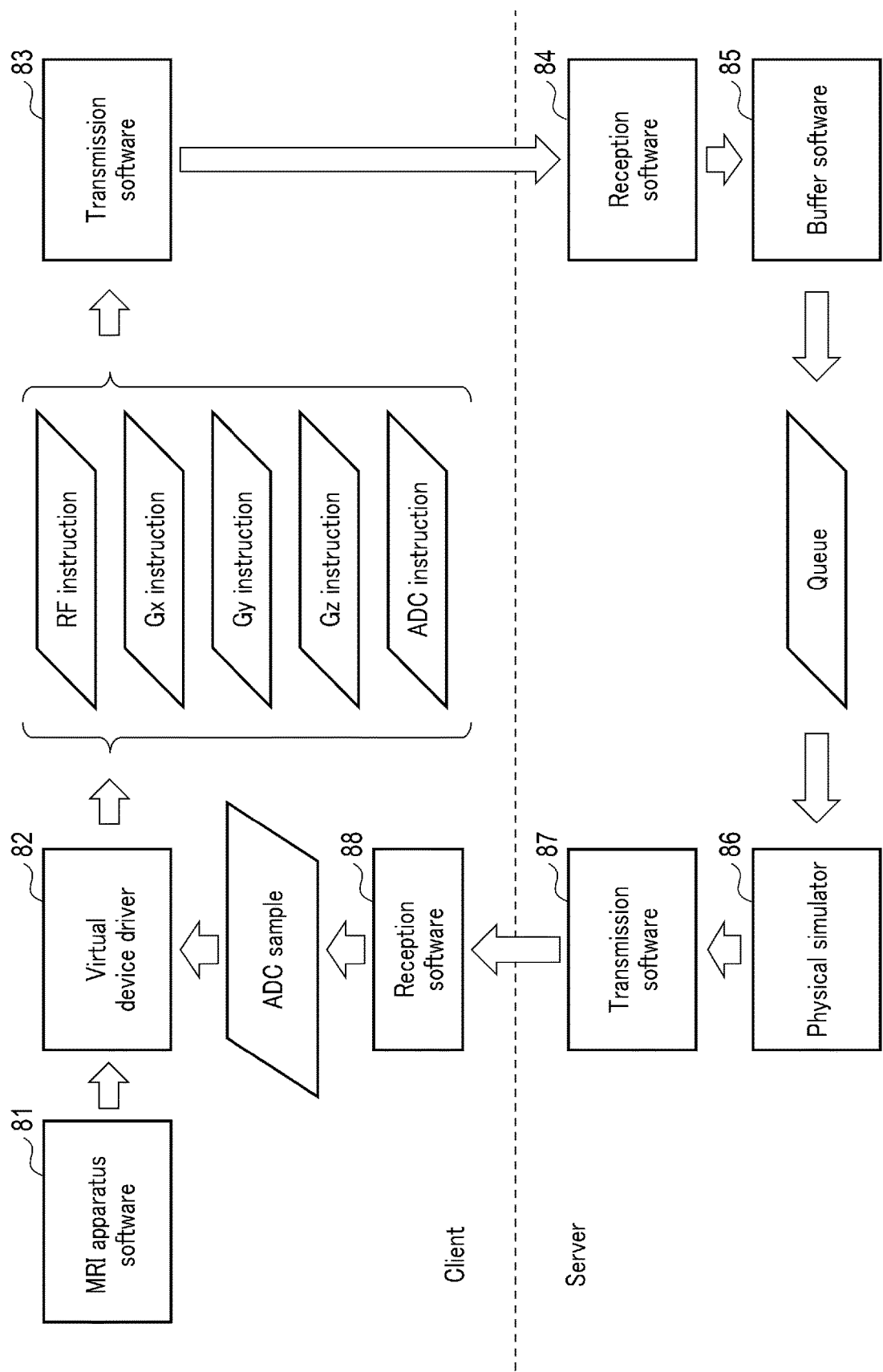
FIG. 8 is a diagram illustrating a software configuration and a flow of various data relating to a Bloch simulation according to Example 1.

FIG. 8 is a diagram illustrating a software configuration and a flow of various data relating to a Bloch simulation according to Example 1. As illustrated in FIG. 8, the Bloch simulation according to Example 1 is implemented by a client-server system. It is assumed that the client is a magnetic resonance imaging apparatus, or a computer emulating the magnetic resonance imaging apparatus, and the server is the physical simulation apparatus 1. In various processors of the client, MRI apparatus software 81, a virtual device driver 82, transmission software 83 and reception software 88 are implemented. In various processors of the server, reception software 84, buffer software 85, a physical simulator 86 and transmission software 87 are implemented.

As the MRI apparatus software 81, use is made of software that is implemented in the host computer 21 of the magnetic resonance imaging apparatus. The MRI apparatus software 81 generates a logical pulse sequence. The virtual device driver 82 is a device driver relating to the hardware control circuitry 22 that controls the above-described hardware 23 of the magnetic resonance imaging apparatus, to be specific, the RF transmitter coil, gradient coil and/or A/D conversion circuitry. To be more specific, as the virtual device driver 82, use is made of software in which the device driver that emulates the hardware control circuitry 22 is modified. The virtual device driver 82 according to Example 1 converts the logical pulse sequence into a plurality of instruction fragments. Specifically, the virtual device driver 82 fragmentally issues, as instruction cross sections, an RF instruction, gradient magnetic field instructions, and an ADC instruction. The RF instruction includes an instruction for the RF transmitter coil. The gradient magnetic field instructions include an instruction for a Gx coil, an instruction for a Gy coil and an instruction for a Gz coil. The ADC instruction includes an instruction for the reception coil. The transmission software 83 transmits the RF instruction, gradient magnetic field instructions and ADC instruction to the server.

The reception software 84 receives the RF instruction, gradient magnetic field instructions and ADC instruction from the client. The buffer software 85 temporarily stores the RF instruction, gradient magnetic field instructions and ADC instruction, which are received by the reception software 84, into the buffer storage device. The physical simulator 86 successively reads out, as a queue, the RF instruction, gradient magnetic field instructions and ADC instruction from the buffer storage device according to the above-described read condition, restores a partial pulse sequence, executes a Bloch simulation by utilizing the partial pulse sequence, and generates an ADC sample. The ADC sample means a predicted output value of the ADC, or in other words, a predicted computation value of k space data. The transmission software 87 transmits the ADC sample to the client.

The reception software 88 of the client receives the ADC sample from the server. Using the reception of the ADC sample as a trigger, the virtual device driver 82 issues a plurality of instruction fragments, and the physical simulator 86 executes the Bloch simulation, based on the queue of the instruction fragments, and generates the ADC sample. In this manner, the issuance of sequence elements and the execution of the Bloch simulation are cyclically repeated.

Example 2

FIG. 9 is a diagram illustrating a software configuration and a flow of various data relating to a Bloch simulation according to Example 2. The same constituent elements as in FIG. 8 are denoted by identical reference signs, and a description thereof is omitted unless otherwise necessary. As illustrated in FIG. 9, in the Bloch simulation according to Example 2, in various processors of the client, MRI apparatus software 81, a virtual device driver 82, buffer software 85 and transmission software 83 are implemented, and, in various processors of the server, reception software 84, a physical simulator 86 and transmission software 87 are implemented.

The MRI apparatus software 81 generates a logical pulse sequence. The virtual device driver 82 fragmentally issues a plurality of instruction fragments of the logical pulse sequence, to be specific, an RF instruction, gradient magnetic field instructions, and an ADC instruction. The buffer software 85 temporarily stores the RF instruction, gradient magnetic field instructions and ADC instruction, which are received by the reception software 84, into the buffer storage device. In Example 2, the buffer storage device is mounted in the client. The transmission software 83 successively reads out, as a queue, the RF instruction, gradient magnetic field instructions and ADC instruction from the buffer storage device according to the above-described read condition, and transmits the RF instruction, gradient magnetic field instructions and ADC instruction to the server.

The reception software 84 receives a queue of the RF instruction, gradient magnetic field instructions and ADC instruction from the client. The physical simulator 86 restores a partial pulse sequence from the queue, executes a Bloch simulation by utilizing the partial pulse sequence, and generates an ADC sample. The transmission software 87 transmits the ADC sample to the client.

The reception software 88 of the client receives the ADC sample from the server. Using the reception of the ADC sample as a trigger, the virtual device driver 82 issues a plurality of instruction fragments, and the physical simulator 86 executes the Bloch simulation, based on the queue of the instruction fragments, and generates the ADC sample. In this manner, the issuance of sequence elements and the execution of the Bloch simulation are cyclically repeated.

Example 3

Figure 10:
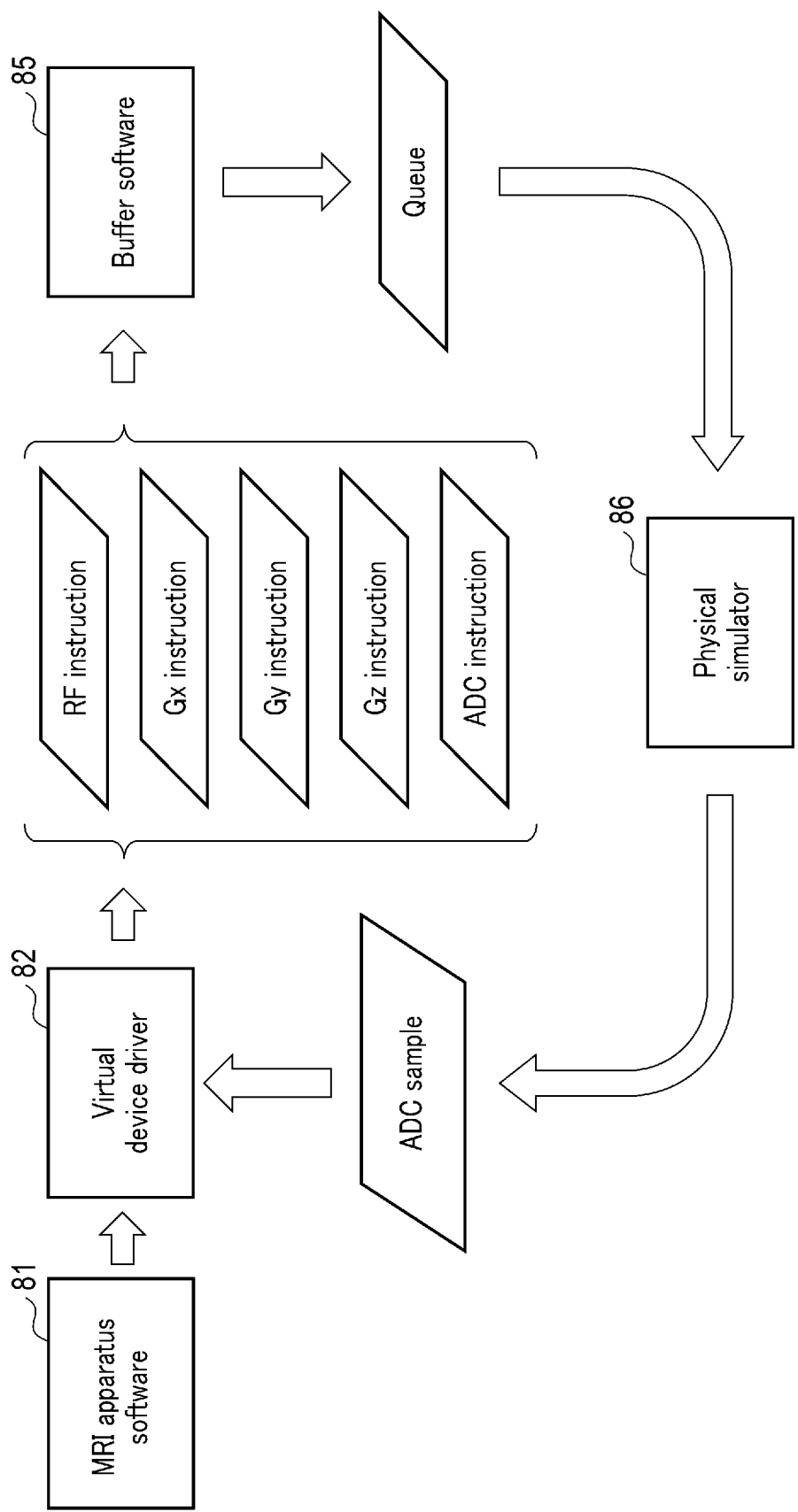
FIG. 10 is a diagram illustrating a software configuration and a flow of various data relating to a Bloch simulation according to Example 3.

FIG. 10 is a diagram illustrating a software configuration and a flow of various data relating to a Bloch simulation according to Example 3. The same constituent elements as in FIG. 8 and FIG. 9 are denoted by identical reference signs, and a description thereof is omitted unless otherwise necessary. As illustrated in FIG. 10, the Bloch simulation according to Example 3 is implemented by a single configuration by a server. In various processors of the server, MRI apparatus software 81, a virtual device driver 82, buffer software 85 and a physical simulator 86 are implemented.

The MRI apparatus software 81 generates a logical pulse sequence. The virtual device driver 82 fragmentally issues a plurality of instruction fragments of the logical pulse sequence, to be specific, an RF instruction, gradient magnetic field instructions, and an ADC instruction. The buffer software 85 temporarily stores the RF instruction, gradient magnetic field instructions and ADC instruction, which are received by the reception software 84, into the buffer storage device. In Example 3, the buffer storage device is mounted in the server. The physical simulator 86 successively reads out, as a queue, the RF instruction, gradient magnetic field instructions and ADC instruction from the buffer storage device according to the above-described read condition, restores a partial pulse sequence, executes a Bloch simulation by utilizing the partial pulse sequence, and generates an ADC sample. Using the reception of the ADC sample as a trigger, the virtual device driver 82 issues a plurality of instruction fragments, and the physical simulator 86 executes the Bloch simulation, based on the queue of the instruction fragments, and generates the ADC sample. In this manner, the issuance of instruction fragments and the execution of the Bloch simulation are cyclically repeated.

In the above-described first and second embodiments, it is assumed that the control target apparatus is the magnetic resonance imaging apparatus. However, the present embodiments are not limited to this. For example, the control target apparatus may be an X-ray computed tomography apparatus. In this case, as the physical simulation, an X-ray CT simulation that simulates X-ray computed tomography may be used, and as the hardware control sequence, use may be made of a control sequence for an X-ray high voltage generating device, an X-ray tube, an X-ray detector and data collection circuitry. In another example, the control target apparatus may be an ultrasonic diagnosis apparatus. In this case, as the physical simulation, an ultrasonic image diagnosis simulation that simulates the ultrasonic diagnosis apparatus may be used, and as the hardware control sequence, use may be made of a control sequence for ultrasonic transmission circuitry, an ultrasonic probe, ultrasonic reception circuitry, B-mode processing circuitry, and Doppler processing circuitry. Aside from the above, the control target apparatus may be other image diagnosis apparatuses that are reproducible by a physical simulation.

The control target apparatus may be an electronic clinical thermometer as an example other than the image diagnosis apparatus. In this case, an electronic clinical thermometer simulation that simulates the electronic clinical thermometer may be used as the physical simulation, and as the hardware control sequence, use may be made of control information of electronic clinical thermometer control circuitry, a thermistor and the like. It suffices if heat conduction is simulated by using a human body model, and a body temperature that is an output result of the electronic clinical thermometer can be calculated. In another example, other than the image diagnosis apparatus, the control target apparatus may be an electronic blood pressure meter. In this case, an electronic blood pressure meter simulation that simulates the electronic blood pressure meter may be used as the physical simulation, and as the hardware control sequence, use may be made of pressure control circuitry or a pressure sensor of a cuff, or pulse wave detection circuitry. In this case, it suffices if pulsation and pressure transfer are simulated by using a human body model, and a blood pressure and a pulse wave that are an output result of the electronic blood pressure meter are calculated. Aside from the above, the control target apparatus may be other medical equipment that is reproducible by a physical simulation.

According to at least one of the above-described embodiments, a physical simulation with a high reproducibility of a hardware behavior can be executed.

The term "processor" used in the above description means, for example, circuitry such as a CPU, GPU, an application specific integrated circuit (ASIC), a programmable logic device (for example, a simple programmable logic device (SPLD), or a complex programmable logic device (CPLD)), and a field programmable gate array (FPGA). The processor implements functions by reading and executing a program stored in the storage circuitry. Note that, instead of storing the program in the storage circuitry, such a configuration may be adopted that the program is directly assembled in the circuitry of the processor. In this case, the processor implements functions by reading and executing the program assembled in the circuitry of the processor. On the other hand, in a case where the processor is, for example, an ASIC, the functions are directly assembled as logic circuitry in the circuitry of the processor, instead of the program being stored in the storage circuitry. Note that the processors in the embodiments are not limited to cases where each processor is constituted as single circuitry, and a plurality of independent circuities may be combined to constitute one processor and to implement functions thereof. Furthermore, a plurality of constituent elements in FIG. 1 to FIG. 7 may be integrated into one processor, and the processor may implement the functions thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A physical simulation apparatus comprising:
   element reception circuitry configured to successively receive sequence elements of a hardware control sequence that is divided according to a division rule on a transmission side;
   a storage device configured to store the received sequence elements;
   storage control circuitry configured to read out the sequence elements stored in the storage device, in a case where a separately determined condition is satisfied; and
   simulation circuitry configured to execute a physical simulation, based on the read-out sequence elements, and to compute a predicted computation value of a signal value that a control target apparatus of the sequence elements collects.

2. The physical simulation apparatus of claim 1, wherein the sequence elements are obtained by dividing the hardware control sequence in a time direction, and/or dividing the hardware control sequence in regard to each of constituent devices included in the control target apparatus.

3. The physical simulation apparatus of claim 1, wherein
   the control target apparatus is a magnetic resonance imaging apparatus, and
   the hardware control sequence is a pulse sequence.

4. The physical simulation apparatus of claim 3, wherein the sequence elements are obtained by dividing the pulse sequence in a time direction, and/or dividing the pulse sequence in regard to each of constituent devices included in the control target apparatus.

5. The physical simulation apparatus of claim 4, wherein the constituent devices include a gradient magnetic field power supply, RF transmission circuitry, and A/D conversion circuitry.

6. The physical simulation apparatus of claim 5, wherein the condition is that a start instruction or an end instruction of sampling by the A/D conversion circuitry is received.

7. The physical simulation apparatus of claim 5, wherein the condition is that a predetermined time has passed since a start instruction or an end instruction of sampling by the A/D conversion circuitry.

8. The physical simulation apparatus of claim 1, wherein the element reception circuitry is connected to a transmission device of the sequence elements via network communication or inter-process communication.

9. The physical simulation apparatus of claim 1, further comprising examination target reception circuitry that is reception circuitry different from the element reception circuitry and receives setting information of an examination target of the physical simulation.

10. The physical simulation apparatus of claim 1, wherein in a case where an elapsed time of the physical simulation is slower than a predetermined time, the simulation circuitry lowers an accuracy of the physical simulation.

11. The physical simulation apparatus of claim 10, wherein in order to lower the accuracy of the physical simulation, the simulation circuitry increases a time step width in the physical simulation.

12. The physical simulation apparatus of claim 1, wherein the sequence elements are generated by a virtual device driver relating to control circuitry that controls RF transmission circuitry a gradient coil and/or A/D conversion circuitry of a magnetic resonance imaging apparatus.

13. The physical simulation apparatus of claim 1, further comprising a medical image diagnosis apparatus as the control target apparatus.

14. A physical simulation method comprising:
    successively receiving, by element reception circuitry, sequence elements of a hardware control sequence that is divided according to a division rule on a transmission side;
    storing, by a storage device, the received sequence elements;
    reading out, by storage control circuitry, the sequence elements stored in the storage device, in a case where a separately determined condition is satisfied; and
    executing, by simulation circuitry, a physical simulation, based on the read-out sequence elements, and computing a predicted computation value of a signal value that a control target apparatus of the sequence elements collects.

* * * * *